(12) United States Patent
Efros et al.

(10) Patent No.: US 11,568,963 B2
(45) Date of Patent: Jan. 31, 2023

(54) METHOD FOR CREATING AND USING REGISTRY OF CLINICAL TRIAL PARTICIPANTS

(71) Applicants: Mitchell D. Efros, Roslyn, NY (US); Kerri Weingard, Dix Hills, NY (US)

(72) Inventors: Mitchell D. Efros, Roslyn, NY (US); Kerri Weingard, Dix Hills, NY (US)

(73) Assignee: Verified Clinical Trials, Garden City, NJ (US)

( * ) Notice: Subject to any disclaimer, the term of this patent is extended or adjusted under 35 U.S.C. 154(b) by 1215 days.

(21) Appl. No.: 15/646,187

(22) Filed: Jul. 11, 2017

(65) Prior Publication Data

US 2017/0308680 A1    Oct. 26, 2017

Related U.S. Application Data

(63) Continuation-in-part of application No. 14/694,271, filed on Apr. 23, 2015, now Pat. No. 10,510,437.

(60) Provisional application No. 62/127,331, filed on Mar. 3, 2015.

(51) Int. Cl.
| | |
|---|---|
| *G16H 10/20* | (2018.01) |
| *G16H 15/00* | (2018.01) |
| *G06F 16/9535* | (2019.01) |
| *G16H 10/60* | (2018.01) |
| *G06Q 40/00* | (2012.01) |

(52) U.S. Cl.
CPC ......... *G16H 10/20* (2018.01); *G06F 16/9535* (2019.01); *G16H 10/60* (2018.01); *G16H 15/00* (2018.01); *G06Q 40/10* (2013.01)

(58) Field of Classification Search
CPC ........ G06Q 30/00; G06Q 50/22; G06Q 30/06; G06Q 10/1097; G06Q 30/02; G06Q 50/01; G06Q 50/00; G06Q 40/00; G06H 10/60; G06F 19/3418; G06F 17/00; G05B 15/02; H04R 3/00; H04L 12/2827; G16H 50/30
See application file for complete search history.

(56) References Cited

U.S. PATENT DOCUMENTS

| | | | |
|---|---|---|---|
| 2004/0006553 A1* | 1/2004 | de Vries et al. | |
| 2006/0184493 A1* | 8/2006 | Shiffman et al. | |
| 2012/0078648 A1* | 3/2012 | Reiner | |

(Continued)

*Primary Examiner* — Michael Tomaszewski
*Assistant Examiner* — William T. Monticello
(74) *Attorney, Agent, or Firm* — Kohn & Associates, PLLC

(57) ABSTRACT

A method of screening participants for a clinical trial by obtaining identifying information chosen from a biometric sample, personal information, physical attributes, and combinations thereof from a prospective participant, optionally generating a unique identifier code, populating a database server with the unique identifier code and participant information and storing the information on non-transitory computer readable media, screening the participant for a clinical trial based on either the unique identifier code and/or participant information and searching for a match with existing participant information in the database server and a plurality of outside databases to determine protocol violations, and determining eligibility of the participant for the clinical trial and preventing the protocol violations. A system for screening participants for a clinical trial and preventing future violations while currently enrolled in a clinical trial.

17 Claims, 10 Drawing Sheets

(56) References Cited

U.S. PATENT DOCUMENTS

2012/0323773 A1\* 12/2012 Lawrence et al.
2014/0136239 A1\* 5/2014 Miller
2014/0222444 A1\* 8/2014 Cerello et al.
2017/0061102 A1\* 3/2017 Weber et al.

\* cited by examiner

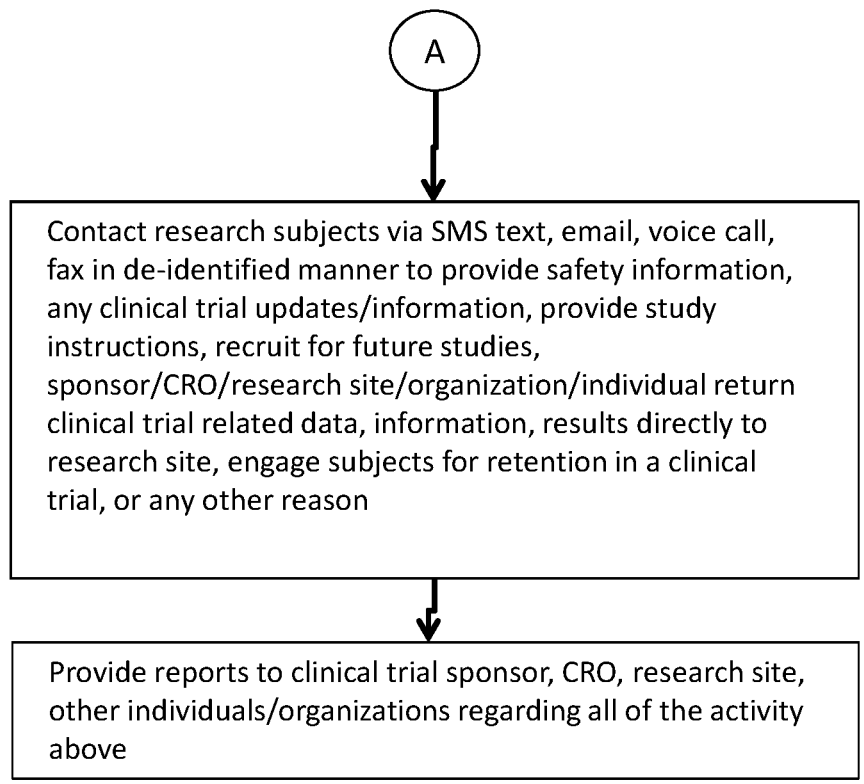
FIGURE 1B con't

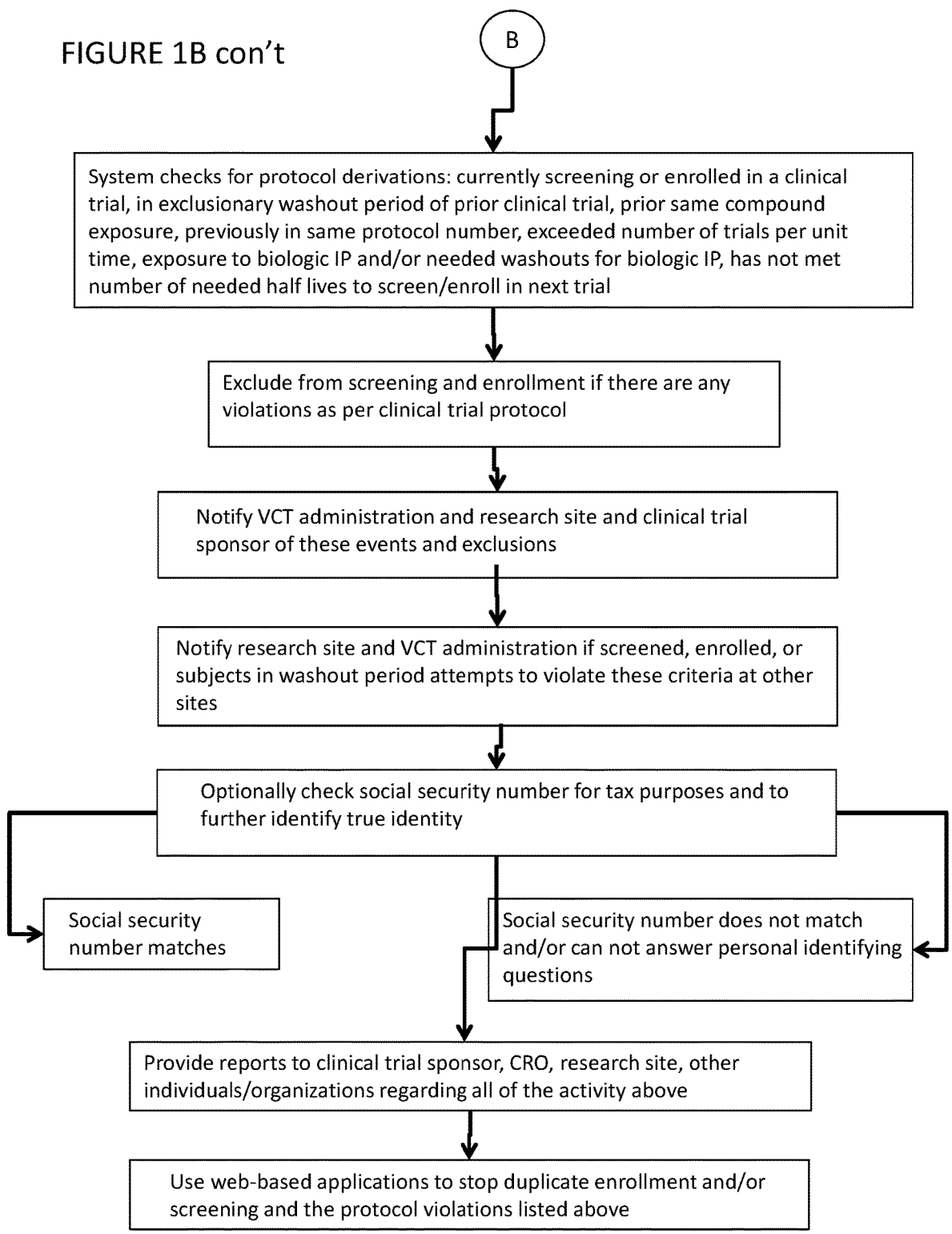
FIGURE 1B con't

METHOD FOR CREATING AND USING REGISTRY OF CLINICAL TRIAL PARTICIPANTS

BACKGROUND OF THE INVENTION

1. Technical Field

The present invention relates to registries of clinical trial participants. More specifically, the present invention relates to methods of preventing participants from enrolling in multiple clinical trials simultaneously, and to perform other types of checks on participants, across all types of drug and device trials in all phases of clinical research.

2. Background Art

There are many research studies conducted by various institutions and companies that make up "clinical trials". These clinical trials are generally used to verify the safety and efficacy of pharmaceuticals, biopharmaceuticals, and medical devices for the FDA. There are many different types of clinical trials, including treatment trials, prevention trials, diagnostic trials, screening trials, and quality of life trials.

The general public can enroll in clinical trials if they meet the criteria of the particular trial, such as having or not having a certain medical condition, currently taking a particular type of medicine, or having certain health characteristics. Clinical trials can be beneficial to many people who have exhausted currently approved treatments for their conditions since they allow such people to seek experimental procedures in order to improve their quality of life. People enrolled in clinical trials must also be aware of their risks, such as side effects and adverse reactions, or the fact that the treatment might not provide any results. There is a lot of motivation for people, especially in bad economic times, to join clinical trials because they are compensated monetarily to receive medical evaluation and care as well as free medication. However, some people try to enroll in clinical trials more than once providing false information, or attempt to screen and enroll in several clinical trials at the same time. This not only can be dangerous to the person's health, but it can result in unreliable data for the organization conducting the trial.

There are several methods currently used for maintaining registries for clinical trials. For example, US Patent Application Publication No. 2008/0052125 to Bennett, et al. discloses a method for maintaining the contact information of an enrollee in a clinical study while maintaining the anonymity of the enrollee from the clinical study sponsor. The method includes: (1) obtaining contact information for the enrollee in the clinical study; (2) entering the contact information into a database; (3) using a contact cascade on a scheduled, periodic basis to contact the enrollee using the contact information from the database to ensure that the contact information is correct; and (4) updating the contact information if a contact is made with the enrollee and the contact information needs to be updated to be accurate. While this method keeps track of contact information, it cannot easily be used to prevent multiple enrollments under false information.

US Patent Application Publication No. 2008/0033658 to Dalton, et al. discloses computers, computer program products, and methods for identifying a plurality of subjects for a clinical trial. A candidate set of molecular profiles in a stored plurality of molecular profiles are identified. Each such profile has measurements for a discriminating set of cellular constituents that match the measurements of corresponding cellular constituents in a responder set of biological samples, thereby identifying the plurality of subjects for the trial from those subjects from which the candidate set of molecular profiles were derived. Each respective molecular profile in the stored plurality of profiles has measurements of a plurality of cellular constituents from a respective biological sample in a plurality of samples obtained from a first plurality of subjects. The discriminating set of cellular constituents is identified from those cellular constituents in the plurality of cellular constituents whose measurement values discriminates between the responder and non-responder sets of biological samples. This method is used to select specific candidates for a particular trial based on their biological samples, but is not used to prevent multiple enrollments.

US Patent Application Publication No. 2010/0023870 to Baker discloses an apparatus and methods that implement a computer-based system and procedure for the efficient and effective operation of one or more clinical trials using an institutional review board (IRB). The various methods are deployed against the backdrop of an Internet-based Software As A Service (SaaS) platform, allowing access to the system by all relevant participants. Each authorized participant in the clinical trial can have a customized and customizable view of the clinical trial and interact with the other participants electronically. The various documents required for completion of the clinical trial or study, as well as the various compliance documents needed to satisfy regulatory agencies are all available for review via the Internet. By utilizing the methods and system of the present invention, greater protection is offered for the human subjects of the clinical trials. Further, the sponsors, investigators, and the study participants can experience increased productivity. Finally, FDA mandated information can be more readily tracked and, accordingly, compliance with FDA guidelines can be enhanced. This method is directed to controlling information pertaining to the trials, but does not prevent multiple enrollments.

US Patent Application Publication Nos. 2005/0159654 and 2003/0130871 to Rao, et al. disclose a system and method for selecting prospective patients for a clinical trial. In various embodiments, a clinical trials brokerage is configured to receive requests from drug companies for lists of persons meeting specified criteria for clinical trials. Patient records are retrieved from a structured computerized patient record (CPR) data warehouse populated with comprehensive patient information mined from unstructured hospital records. A list of persons for whom consent was obtained can be outputted and forwarded to the entity interested in performing the clinical trial and which requested the list. Anonymity of a patient can be maintained until the patient provides consent to participate in the clinical trial. This method also does not provide any secure means of preventing multiple enrollments in trials.

US Patent Application Publication No. 2004/0006553 to de Vries, et al. discloses a method of conducting clinical trials over a network (e.g. the Internet or telephone grid). All trial participants and all trial investigators are asked to provide a baseline biometric reading, consisting of one or more of voiceprint, fingerprint, iris scan, electronic signature or other biometric modality, along with one or more identifiers such as their name, a user name and password combination, etc. The provided biometric information and identifiers are then permanently recorded into the biometric consent database. This biometric consent database is then used to obtain informed consent verified with biometric authentication from the enrolled trial participants and investigators. A unique code can be assigned to each trial participant. This method does not provide any way to maintain the integrity of a trial and prevent multiple enrollments or protocol violations.

US Patent Application Publication No. 2010/0185462 to Lungescu, et al. discloses Clinical RSVP, a web-based subject registry used by investigators to make better-informed enrollment decisions for clinical research studies. Research sites can report dose dates of subjects for the purpose of identifying ineligible subjects and ensuring against dual enrollment. Fingerprint biometric identification (or other biometric information, such as iris, retinal, or facial recognition or DNA) can be used along with other identifying information such as initials, birth date, sex, and last four digits of a social security or tax ID number. The subject is fingerprinted when screened for the trial, the fingerprint is then scanned, and a code is generated and stored in a database along with the other identifiers. The registry is searchable for a subject's information. Clinical RSVP is used for phase I trials. There are several disadvantages of using biometric fingerprint technology with this system. Firstly, the technology does not function accurately in a significant percentage of cases. Many senior subjects or laborers are especially prone to problems with this technology as the system has difficulty reading the fingerprints. To supply all research sites in the country is not only expensive, but remains impractical and problematic as well. There are hardware and software installations required with this technology, which adds cost and time. When problems are encountered with fingerprint scanning, it slows down the entire screening process. Many potential research subjects have concerns about leaving biometric information with the research site. Clinical RSVP remains focused on early phase studies as providing fingerprint scanners to every research site across the country would be too expensive and time consuming. Clinical RSVP therefore does not have penetration to later phase studies, and does not prevent other key protocol violations, and many subjects are known to cross between phase 1 studies and later phase studies.

While many of the above described systems can generate databases of prospective participants in clinical trials, there is no unified system to stop research subjects from enrolling in more than one clinical trial at a time across all phases of clinical research and all therapeutic areas in both device and/or drug clinical trials, or waiting the mandated waiting time or washout period between clinical trials, exclusionary criteria that are listed in most drug and device clinical trials. There are also current problems prohibiting an effective clinical trial registration because of the lack of a system and protocol that respects patient privacy while handling a wide array of patient information. Furthermore, there is no system that has the ability to analyze multiple databases in which patient data can be found in order to provide a thorough screen for a clinical trial to prevent protocol violations. There currently exists no synthesized and query-able dataset that could perform the operations needed for a complete search of relevant clinical trial data. Even complete electronic health/medical records do not contain all of the information needed to determine if a patient qualifies for a clinical trial. It is not technically feasible to search all existing outside databases 'on-demand' when evaluating whether or not they qualify for a study. Also, such a method could not be performed by humans. The study participation history and personal information as well as biometric information cannot be shared across medical offices, across research sites, research units, CROs, nor with the sponsor of the clinical trial. Therefore, there remains the need for an improved screening system to prevent duplicate enrollment and protocol violations for clinical trials to reduce costs of clinical research and improve clinical research safety and data quality with the ability to search a plurality of databases containing patient information as well as create a de-identified method to check study participation history across multiple sites and companies.

SUMMARY OF THE INVENTION

The present invention provides for a method of screening participants for a clinical trial by obtaining identifying information chosen from a biometric sample, personal information, physical attributes, and combinations thereof from a prospective participant, populating a database server with the participant information and storing the information on non-transitory computer readable media, screening the participant for a clinical trial based on the participant information and searching for a match with existing participant information in the database server and a plurality of outside databases to determine protocol violations, and determining eligibility of the participant for the clinical trial and preventing the protocol violations.

The present invention also provides for a system for screening participants for a clinical trial, including an electronic database server in electronic communication with a server instance for collecting participant information on non-transitory computer readable media, said server instance including a screening mechanism for determining eligibility of the participant for the clinical trial and preventing protocol violations and being in electronic communication with a plurality of outside databases.

DESCRIPTION OF THE DRAWINGS

Other advantages of the present invention are readily appreciated as the same becomes better understood by reference to the following detailed description when considered in connection with the accompanying drawings wherein.

DETAILED DESCRIPTION OF THE INVENTION

The present invention generally relates to methods of screening prospective patients and preventing multiple enrollments by searching multiple databases for participant information. The present invention also relates to the use of biometric identification techniques, such as DNA identification, to allow for accurate screening for clinical trials in order to improve the reliability of data obtained while maintaining the confidentiality of the prospective and actual participants. The present invention also relates to determining eligibility of prospective participants in a trial and preventing protocol violations that can possibly affect safety and data quality of a clinical trial. The present invention is particularly suited to prevent persons from enrolling in multiple or repeated clinical trials under false identities for collecting remuneration.

Figure 5:
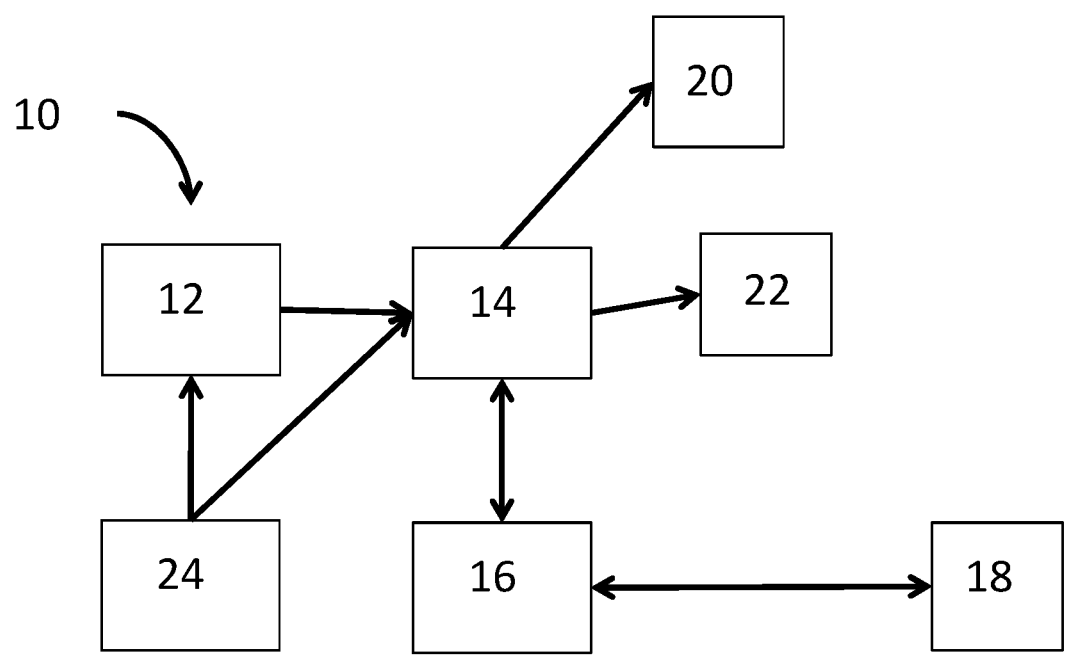
FIG. 5 is a depiction of the flow of information and components in the system of the present invention.

Most generally, the present invention provides for a system 10 for screening participants for a clinical trial, including preferably a unique identifier code generator 12, an electronic database server 14 for storing unique identifier codes generated (if generated) and participant information on non-transitory computer readable media, and a screening mechanism 16 for determining eligibility of the participant for the clinical trial and preventing protocol violations. The unique identifier code generator 12 is an optional component. The screening mechanism 16 is in electronic communication with multiple outside database servers of patient information 18. The system 10 prevents duplicate enrollment and protocol violations but also can obtain status updates by communicating to IVRS/IWRS and multiple databases. However, the prevention of protocol violations is within the system 10 as clinical trial sites enter each prospective participant in the registry. This system 10 is further described in the method below and shown in FIG. 5, FIG. 6, and FIG. 7.

The present invention also provides for a method of screening participants for a clinical trial by obtaining identifying information chosen from a biometric sample, personal information, physical attributes, and combinations thereof from a prospective participant, optionally generating a unique identifier code, populating a database server with the unique identifier code if generated and participant information and storing the database on non-transitory computer readable media, screening the participant for a clinical trial based on the unique identifier code if generated and participant information and searching for a match with existing participant data in a plurality of databases to determine protocol violations, and determining eligibility of the participant for the clinical trial and preventing the protocol violations. The method has the technical effect of helping determine which prospective participants are eligible to participate in the clinical trial in order to populate the clinical trial.

Figure 1A:
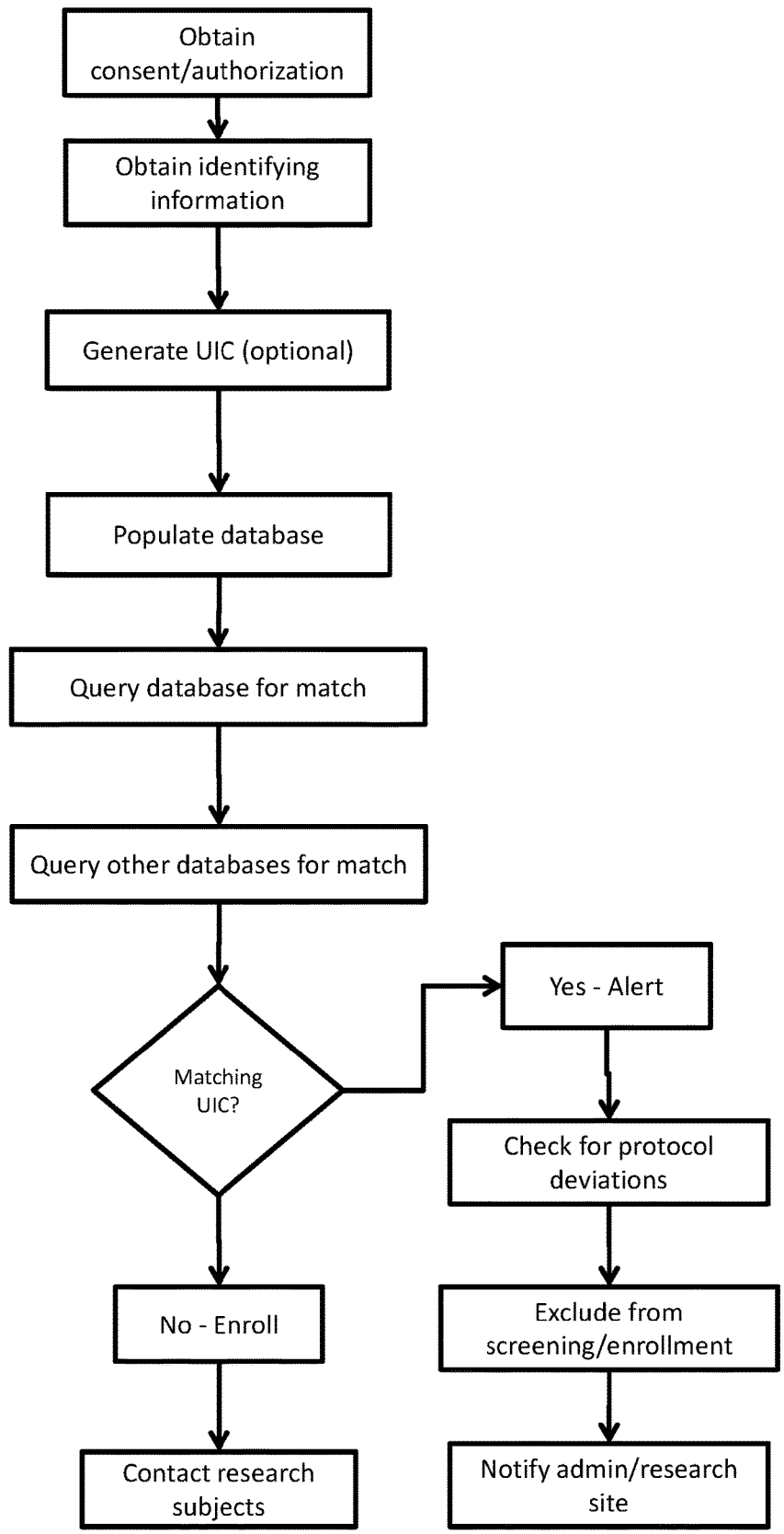
FIG. 1A is a flow chart of the general method of the present invention.
Figure 1B:
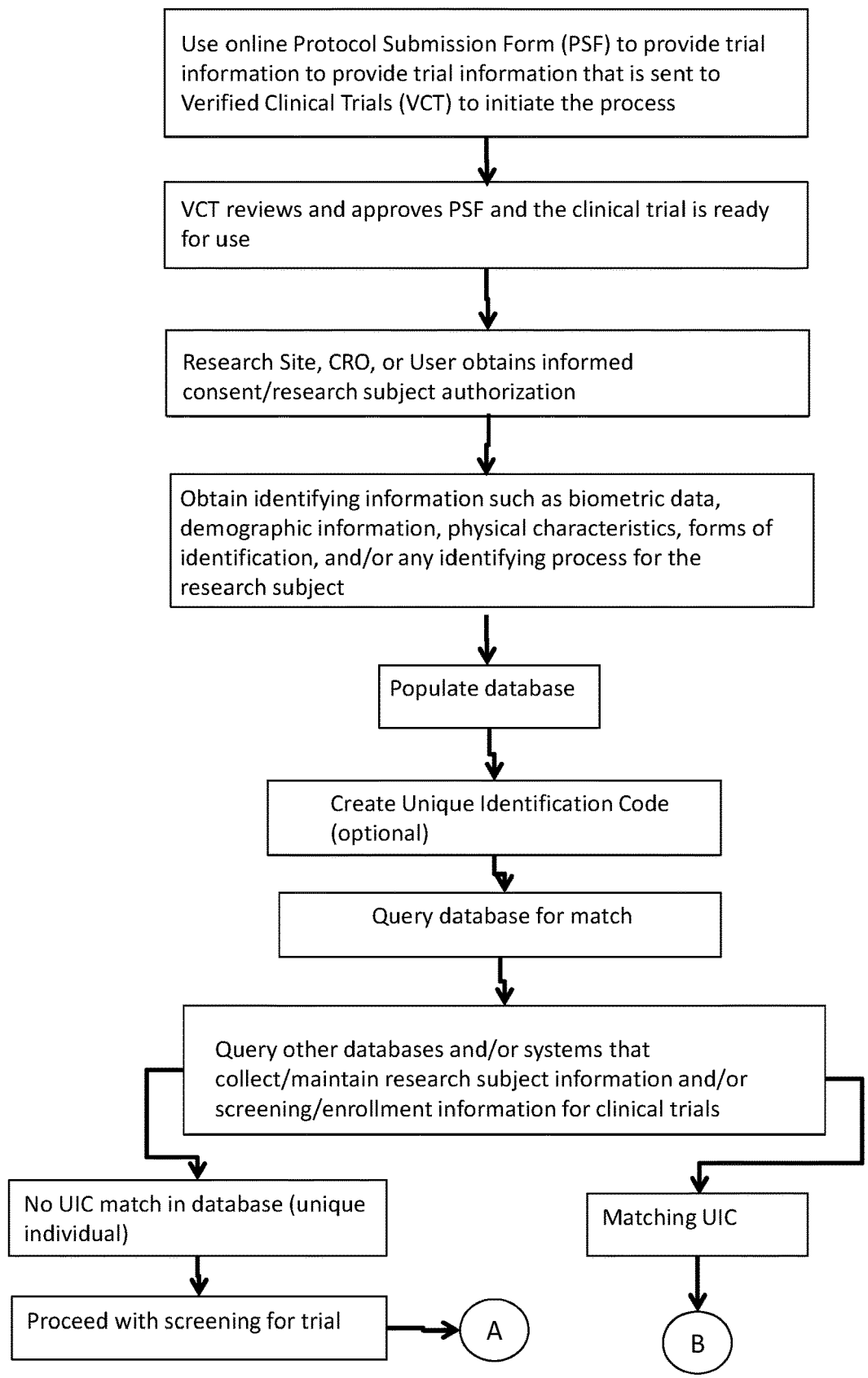
FIG. 1B is a flow chart of more specific steps of the method.
Figure 7:
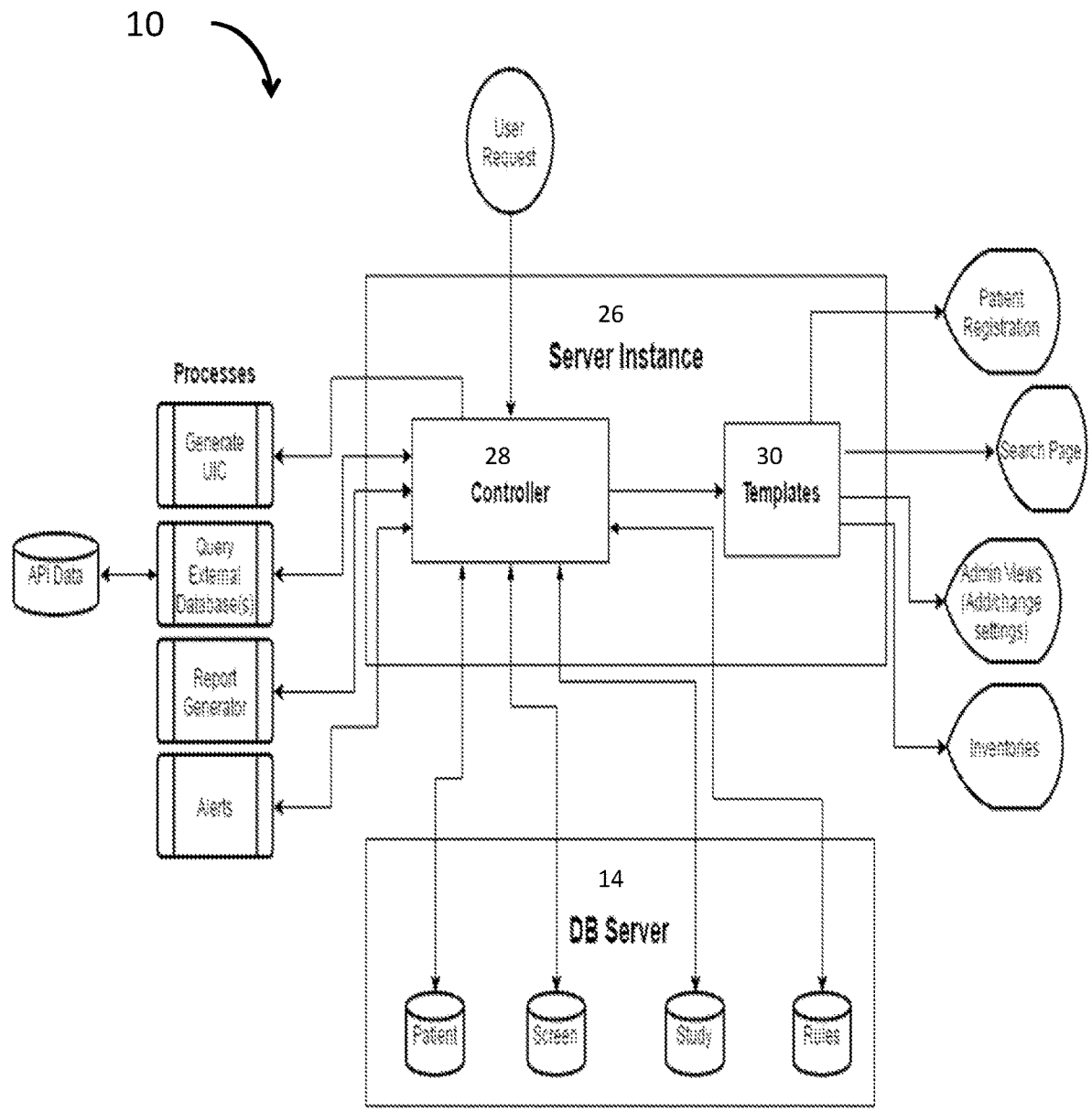
FIG. 7 is a flow chart of processes in the present invention.

The method, generally shown in FIGS. 1A and in more detail in FIG. 1B and FIG. 7, can first include the steps of obtaining consent or authorization of the prospective participant, obtaining identifying information from the prospective participant, optionally generating a unique identifier code for the prospective participant with the unique identifier code generator 12, populating a database server 14 with the unique identifier code and participant information and storing the information on computer readable media, and screening the participant for a clinical trial based on the (optional) unique identifier code and participant information with the screening mechanism 16 and searching for a match with participant data on the database server 14 and multiple outside databases 18.

The identifying information from the prospective participant can be biometric data or information, or a combination thereof. When a prospective participant applies to be in a clinical trial, consent is obtained to collect and use personal information and/or biometric information to be screened for the clinical trial. A biometric sample can be taken from them to add to/compare with other samples in the databases. The biometric sample can be a tissue sample that can be analyzed for DNA, RNA, or any other unique biological identifier. Because everyone has a unique DNA profile, this can be used to identify participants with greater accuracy than by taking their name and government assigned information. The sample can be hair or a body fluid such as saliva, urine, blood, or plasma. The sample can also be obtained by a cheek swab. The biometric sample can also be an iris scan, a voice recording, photograph or picture for face recognition, fingerprints, palm vein scans, or any other type of biometric information. Any combination of the above biometric samples can be used. A biometric sample obtaining mechanism 24 can be used to obtain any of the biometric samples listed above (such as, but not limited to, a fingerprint scanner, a camera, an iris scanner, a voice recorder, a video camera, or any other type of scanner) and can be in electronic communication with the unique identifier code generator 12 and the electronic database server 14.

A unique identifier code (UIC) associated with the prospective clinical trial participant can optionally be generated based on the personal demographic information and also associated with the biometric sample and be stored in the database server 14. The UIC provides a de-identifying method of identifying a participant. The UIC is a reproducible algorithm that is a 64 alphanumeric code that is based on the personal information. When the participant presents to the research facility again, the UIC is detected as an identical match within the database server and the research site would have the dates of his eligibility. If the participant is not beyond the allotted or specified time window of study completion or termination, then that participant is not eligible to participate in the study. If it is more than the needed time frame, the participant can enter the next clinical trial provided they meet all of the study specific eligibility criteria.

The unique identifier code can use a subset of personal demographic information (i.e. personal information), such as, but not limited to, first name, middle name, last name, date of birth, gender, and government issued identification (social security number, tax ID number, driver's license number, passport number, or any other form of government issued ID), or combinations thereof and/or a subset of personal physical attributes and characteristics (i.e. physical attributes), such as, but not limited to, height, weight, hair color, facial recognition, eye color, or combinations thereof. Any other personal information can also be used. In other words, a biometric sample does not need to be taken for the identifying information, and instead personal information and/or physical attributes are obtained from the participant in order to generate the unique identifier code. It should be understood that any combination of these identifying information can be used. Using multiple types of information can ensure the prevention or duplicate or multiple simultaneous enrollment in clinical trials.

Social security numbers and tax ID numbers can also be obtained, entered into the database server 14, and checked instantaneously at the screening to assure that subjects are responsible for the taxes incurred for stipend disbursements and/or further confirm the participant's true identity. Third party software can be used to validate government identification, and can also be used to check criminal backgrounds/sex offender status in order to prevent potentially dangerous individuals from being confined with other inpatients during a study. The unique identifier code generated protects the participants' true identities and is HIPAA and GCP compliant.

An IVRS (interactive voice response system) or an IWRS (interactive web response system) can be used (or any other suitable system that collects identifiers in clinical research, such as IXRS® (Almac)) that uses initials and identifiers to detect duplicate enrollment or protocol violations in order to collect any prospective participant information. Any information collection methods in the process can be web-based, as well as any forms or reports submitted as described herein. Furthermore, commercially available ID scanners can be used to rapidly and accurately assess the validity of the subject's ID and can import that data to the systems database.

Figure 6:
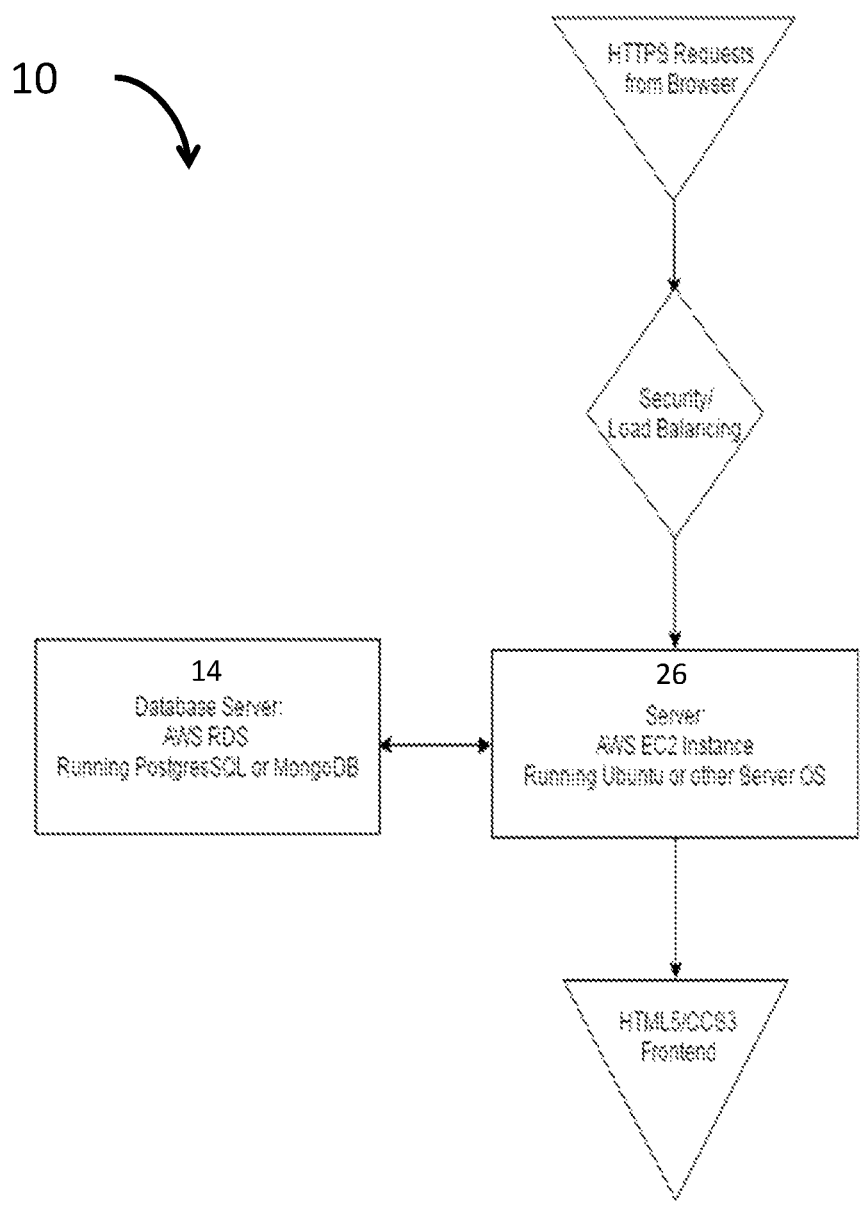
FIG. 6 is a flow chart of information between a database server and instance server.

The database server 14 and its relation to other parts of the system 10 can be seen in FIGS. 6 and 7. The overall system infrastructure is shown in FIG. 6. A server instance 26 is separate from the database server 14 and generally controls the flow of information in the system 10. It is best practice for database-dependent applications to have the database server separate from the main application server because if any technical or security issue should comprise the main application server, the database server remains intact. The server instance 26 can be a virtual server such as those run through Amazon Web Services (AWS), Microsoft Azure, or a custom physical server. The server instance 26 is able to run MVC (model, view, controller) application frameworks such as .NET MVC, Ruby on Rails, Django, Flask, or other suitable programs. Most preferably, the server instance 26 uses Elastic Compute Cloud (EC2) offered through AWS, running the Flask framework. The server instance 26 includes a controller 28 to direct the flow of information in the system 10. The controller 28 processes incoming user requests, and receives and sends information to the database server 14 such as patient information, screen information, study information, and rules. The controller 28 sends information to various processes such as generating a UIC, querying external databases, report generating, and generating alerts. The controller 28 also sends information to a template 30 that can generate various user-friendly screens to enter information for patient registration, search pages, administrative views for adding or changing settings, and inventories.

The database server 14 can be any SQL database or data store that supports encryption such as, but not limited to, MSSQL, MySQL, PostgresSQL, or MongoDB. Preferably, the database server 14 is a Relation Database Service (RDS) offered through AWS running a PostgresSQL server.

The information in the database server 14 through the use of an appropriate template 30 can be viewed on any type of screen (computer monitor, smart phone screen, tablet, or any other wireless device). The database server 14 can be an existing database that can be accessed by any organization or one created by the particular organization for their particular clinical trial or set of clinical trials. Access to the database server 14 can be via a remote connection (wireless, Bluetooth) or a wired connection. Fields of the database server 14 are populated with the participant's biometric identifying information (and unique identifier code if generated) along with any other relevant information about the participant, such as, but not limited to, their history of participation in other clinical trials, status of current enrollment or prospective enrollment in clinical trials, the study start and end dates of the other clinical trials, the sponsor and sponsor information for the other clinical trials, and the trial site, contact person, protocol identifier, study number, and combinations thereof. The database server 14 is secure, and while a participant can delete their personal information from the database server 14, the database server 14 stores the unique identifier code for the screening step.

After the information for the prospective participant is added to the database server 14, it can be compared with existing information in the database server 14 in the screening step with the screening mechanism 16 (controlled by the server instance 26). In other words, a search for a match with existing participant information is performed, as detailed further in Example 1, based on the unique identifier code and/or the identifying information obtained from the prospective participant. If an individual is found with matching unique identifier codes or information to existing information, an alert can be made that the prospective participant is potentially enrolling in the trial multiple times, enrolling in multiple trials at once, or enrolling in a trial sooner than the specified mandatory washout period between clinical trials.

Information can also be compared with any other outside existing databases 18 and/or systems that collect or maintain research subject information and/or screening and enrollment information for clinical trials, such as, but not limited to IVRS/IWRS databases, screening/dosing logs, any clinical trial management system (CTMS) of any kind, databanks that have research subject information, databanks that have information regarding drug/medication use, blood product donation databases of any kind, sperm banks, or any human by-product database. Therefore, the system 10 of the present invention can communicate electronically with other outside existing databases of clinical trial participants or other medical-related databases to cross-reference participant information. This also ensures that protocol violations do not take place. The system can look at non-research patient bases and populations as well so that past non-trial activity can be used to exclude patients from a study or exclude research subjects from blood-product donation, sperm donation, etc.

In order to search and compare information in outside databases 18, queries are performed on each outside database 18 individually. Depending on the database, there can be different search requirements and parameters. A custom communication protocol/standard can be used. The server instance 26 takes parts of the prospective participant's information and maps them appropriately so they can be used as a search. Any dataset containing matches on the given prospective participant returns requested data so it can be added to the main database server 14. Since different software uses different data structures and parameters, the data mapping stage is tedious but once setup enables quick and secure access. Overall, the server instance 26 is able to pull, access, and unify all the data in the database server 14 and the existing outside databases 18 in order to screen the prospective participant. As shown in FIG. 7, the server instance 26 pulls all data in the electronic database server 14 as well as the outside databases 18 and unifies the data in order to screen the data.

Based on the prospective participant's information and comparing with other information in the screening step, it can also be determined if the prospective participant is violating protocol of the clinical trial because of past study screening and enrollment, past investigational compound exposure, or past study history. More specifically, protocol violations (or deviations) can be searched for in both the database server 14 of the present invention and also in a plurality of existing outside databases 18 (especially existing clinical trial databases) that the database of the present invention is in communication with using any of the identifying information obtained above for the participant. In other words, the searching mechanism can search within any outside database 18 that is in communication with that of the present invention in order to find the protocol violations.

These violations can include if the violation is due to the prospective participant currently being in-screening or enrolled at the same or another research site, if they are violating the required number of half-lives since the last research trial, if they are violating the washout period in between trials, if they are violating a biologic modifier washout period, if they have been previously exposed to the same investigational compound if exclusionary per the protocol, if they have exceeded the maximum number of clinical trials per period of time, if they already were a screen failure for the same trial if exclusionary, if they have a blood draw violation (i.e. amount of mL/cc or volume or date of last blood draw is in violation of protocol), if they have a plasma draw violation (i.e. amount of mL/cc or volume or date of last plasma draw is in violation of protocol), and if their last visit is in violation of protocol. If any one or more of these protocol violations are found, the prospective participant can be determined to be ineligible for the clinical trial. In other words, the information can be used to prevent clinical trial protocol violations and potential safety issues based upon a prospective participant's prior screening or enrollment at various other clinical trials. Unlike other methods of screening candidates, the present invention is able to determine violations for any and all of the above reasons, not just a single reason and covers all therapeutic areas and all phases of clinical research by searching through many existing clinical trial databases and other databases that include participant information.

Any additional information can be obtained by the prospective participant in order to search for the protocol violations, such as, but not limited to, past drugs used, past doses of drugs, dates of drug use, dates of visiting a clinical trial research site, or drug half-lives. The searching mechanism can also include requirements for the particular clinical trial being screened (i.e. what drugs would react adversely with the current trial, time periods required to be free of certain drugs, etc.) to compare with any information found regarding the prospective participant in order to determine whether a protocol violation exists.

In the example of blood draw and plasma draw violations, the system 10 of the present invention can be in electronic communication with blood donation center (blood bank) and plasma donation center databases to search for violations. Typically research subjects are not allowed to donate plasma or blood products to blood banks. When using investigational compounds, this can be dangerous as recipients of these blood products and plasma can be exposed to investigational compounds. The system 10 of the present invention can link with blood donation and plasma donation centers in order to notify them of their study status and washout times with all the same alerts as above. The system 10 of the present invention and the outside databases 18 of the blood and plasma donation centers can communicate electronically to one another to notify blood and plasma donation centers of donation from research subjects or to prevent research subjects from participating in trial if they recently donated blood, blood products, or plasma and the amount donated. Communication with the blood and plasma donation centers can be performed at any point in the participant's involvement with a study, and not just during screening.

The database server 14 can detect matching information within seconds to identify potential conflicts and send notifications to relevant individuals by electronic methods (i.e. email, SMS, text, phone) or written methods. If a subject is a "Verification Failure", the research site coordinator is immediately aware and can inform the subject. If any one or all of the protocol violations are found, the research site can be notified immediately. If there is a conflict whereby the subject states that this information is not correct, then the research coordinator can contact higher administration for immediate exploration and resolution of the problem by contacting the prior research site. Any verified clinical trial administration and research site and clinical trial sponsor can be notified of the results of the database comparison. Furthermore, any research site and verified clinical trial administration can be notified if screened, enrolled, or subjects in washout periods attempt to violate protocol at other sites. Also, any research site, verified clinical trial administration, or administration of other databases of medical information (i.e. blood bank or sperm bank administration) can be notified if a subject that is in screening or randomized at a research site/unit has attempted to screen or randomize elsewhere or is attempting to donate blood products, sperm, or any other physiologic product. The system also has the ability for any administrator to obtain notifications and act on them by clicking a link to change the subject's status at their site or send notification to administrators of the system to update the status.

The administration can fully review the information provided by the prospective participant to determine if they should be included in the clinical trial. By catching potential multiple enrollees or unqualified enrollees, the organization can prevent repeated and false data and other problems from occurring during the clinical trial. This can save the pharmaceutical sponsor money by preventing costly screenings and clinical trial enrollment of poor quality subjects. Furthermore, an investigational compound may falsely seem to have adverse events or serious adverse events that might not be caused by the investigational product if taken at the correct dose or not combined with our investigational agents. Moreover, the investigational agent may appear to have a falsely elevated placebo rate if poor quality subjects join a trial for the wrong reasons and never take the product but provide false answers. This could result in making the agent appear not be efficacious or safe resulting in significant loss of IP and money.

Any verification failures can also generate a blacklist or hold list with prospective participant information that prevents poor quality subjects with certain infectious diseases, medical conditions, or behaviors to be excluded from research studies, blood donations, plasma donations, or sperm donations. Such blacklists or hold lists can be communicated electronically to other clinical study databases, blood donation centers, plasma donation centers, and sperm donation centers.

Otherwise, if no matching information is found, the participant can be entered into the clinical trial. If there is no conflict, the research coordinator can obtain a "Verification Success" certificate generated by the system and place this in the source document.

The sponsor of the clinical trial can see screening, enrollment, and other completion activity logs in real time.

The system 10 can include a visit reminder feature to send SMS text phone calls, and/or email to remind subjects of their upcoming visits to reduce out of window visits (late appointments) and subsequent protocol violations. Every time that a reminder is sent out, this can include instructions for their upcoming visit. This can help ensure that the subject is properly prepared for their upcoming visit.

Reports of any of the information in the database server 14 can be created as desired with a report generating mechanism 20. For example, reports of prospective participants who attempt to enroll in multiple clinical trials at once or for the same trial twice can be generated. Reports can be provided to the clinical trial sponsor, CRO (contract research organization), research site, or any other individuals or organizations. Reports regarding attempted simultaneous enrollments are important to know in an effort to gauge the problem within the industry as well as to let the sponsor and CRO know the value of the service. Generation of reports provides a technical effect whether the reports are printed or electronic.

Any prospective participant or participant that is enrolled in a clinical trial can opt to receive and be contacted directly in a de-identified manner about various clinical trial-related communications via email, mail, text, SMS, voice call, voicemail, or any other communication method with a communication mechanism 22. These communications can include, but are not limited to, safety communications, new study related instructions, IRB approved recruitment for new studies, data or study results (general or specific) with regards to dose and efficacy of the investigational treatment, engagement of the participant, or combinations thereof.

In performing the method, a protocol submission form (PSF) can be used. The PSF can be manual or online (web-based). A trial can be built with the database. The PSF can obtain information such as, but not limited to, protocol name and/or number, compound, half-lives of the IP, study start dates, required wash-out dates, is the IP a biologic compound, number of days between screening and randomization, end of study, and last visit date.

The method can further include collecting via email, fax, or any other method and use of screening number and randomization numbers given by the CRO, site, or sponsor clinical trial (such as but not limited by IVRS/IWRS) to update study status as participants move from in screening to randomization and study completion as it applies to protections against all of the protocol violations and duplicate enrollment.

The system 10 can be used to make warning lists or "hold lists" by the research site or clinical pharmacology unit to prevent poor quality subjects from entering in to more of their trials. This list will automatically warn the user at the time of verification.

The system 10 can report subjects that are in screening periods more than 30 days or are "dual screeners" attempting to screen at more than one site at a time.

The system 10 can send out automatic notices to the research site if a subject in screening or enrolled at their site is attempting to screen somewhere else. The site has the ability to update the subject's status directly from this email with a link to the Verified Clinical Trials site.

The system 10 can run reports on all types of protocol violations and status's of the research subjects. The system has a built in dosing calendar to send out reminders on which day dosing will occur.

There are several advantages of the present invention. The unique identifier code is reproducible and can catch minor variations of the information in cases of different forms of identification being used to create the unique identifier code or when there is human error with data entry. The method and system can be used for all phases of studies in all types of disease entities for drug and device trials. The method and system can detect and prevent many types of protocol violations described above that previously have taken too much time or that companies previously have not had enough participant information to detect. This improves clinical trial safety for the potential participant thereby reducing adverse events and serious adverse events. It also promotes improved clinical trial data to the Sponsor and ultimately the consumer. The process reduces placebo events and thereby saves the pharmaceutical sponsor money.

Also, because of HIPAA compliance, the only human that can legally touch the data collected in the database server 14 is the research site personnel that is observing and taking measurements for a current clinical trial. During a new trial, when the screen is run to check the prospective participant's eligibility, the humans running the screen can only receive a "yes" or "no" answer for the eligibility, under HIPAA compliance they are not allowed to know the reason why they are in violation of protocol. The prospective participant's consent obtained at the beginning of the method is critical because it allows the system to look at their personal information.

The invention is further described in detail by reference to the following experimental examples. These examples are provided for the purpose of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLE 1

Figure 2:
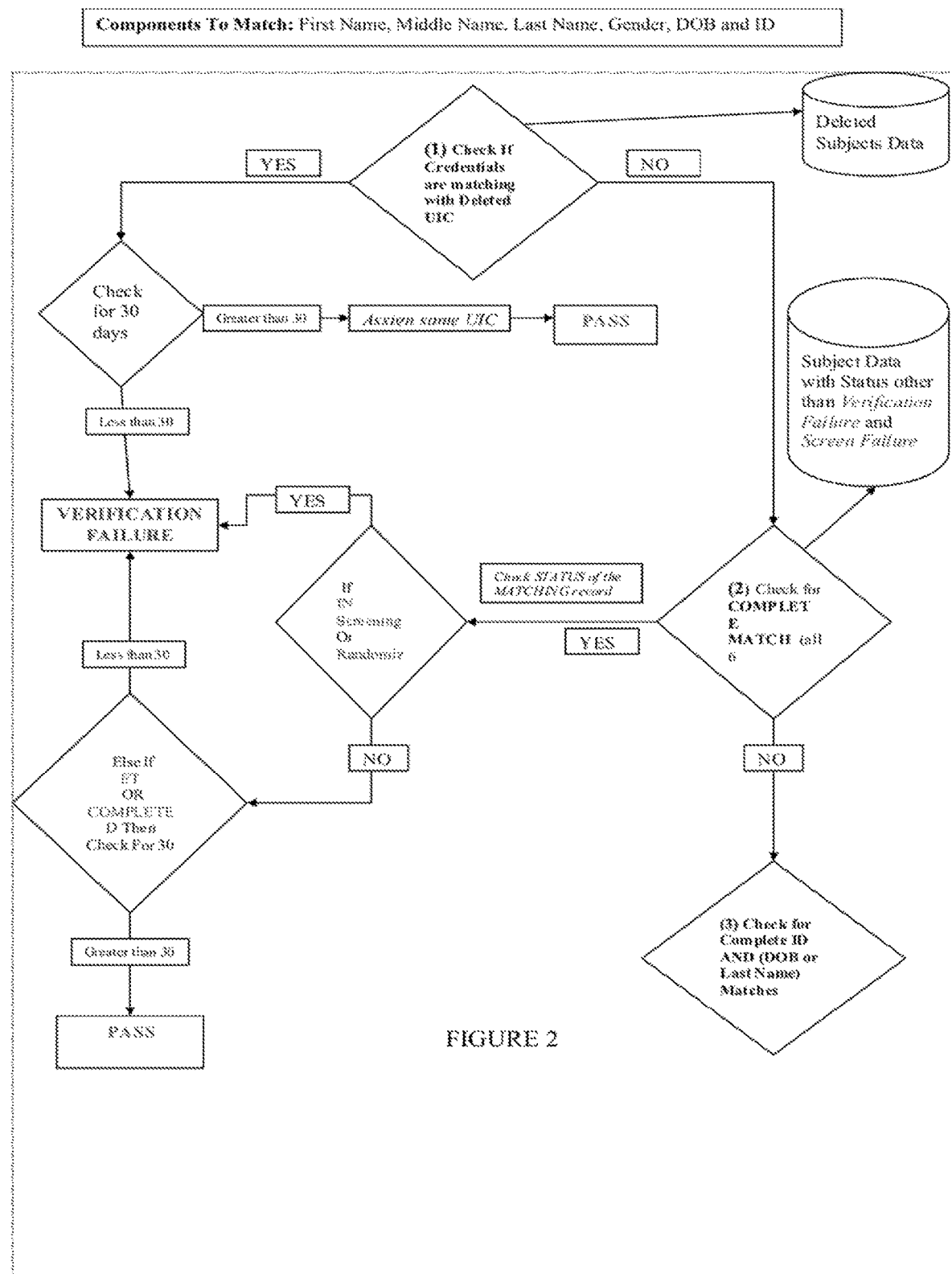
FIG. 2 is a flow chart of steps of the method of checking participant credentials.
Figure 3:
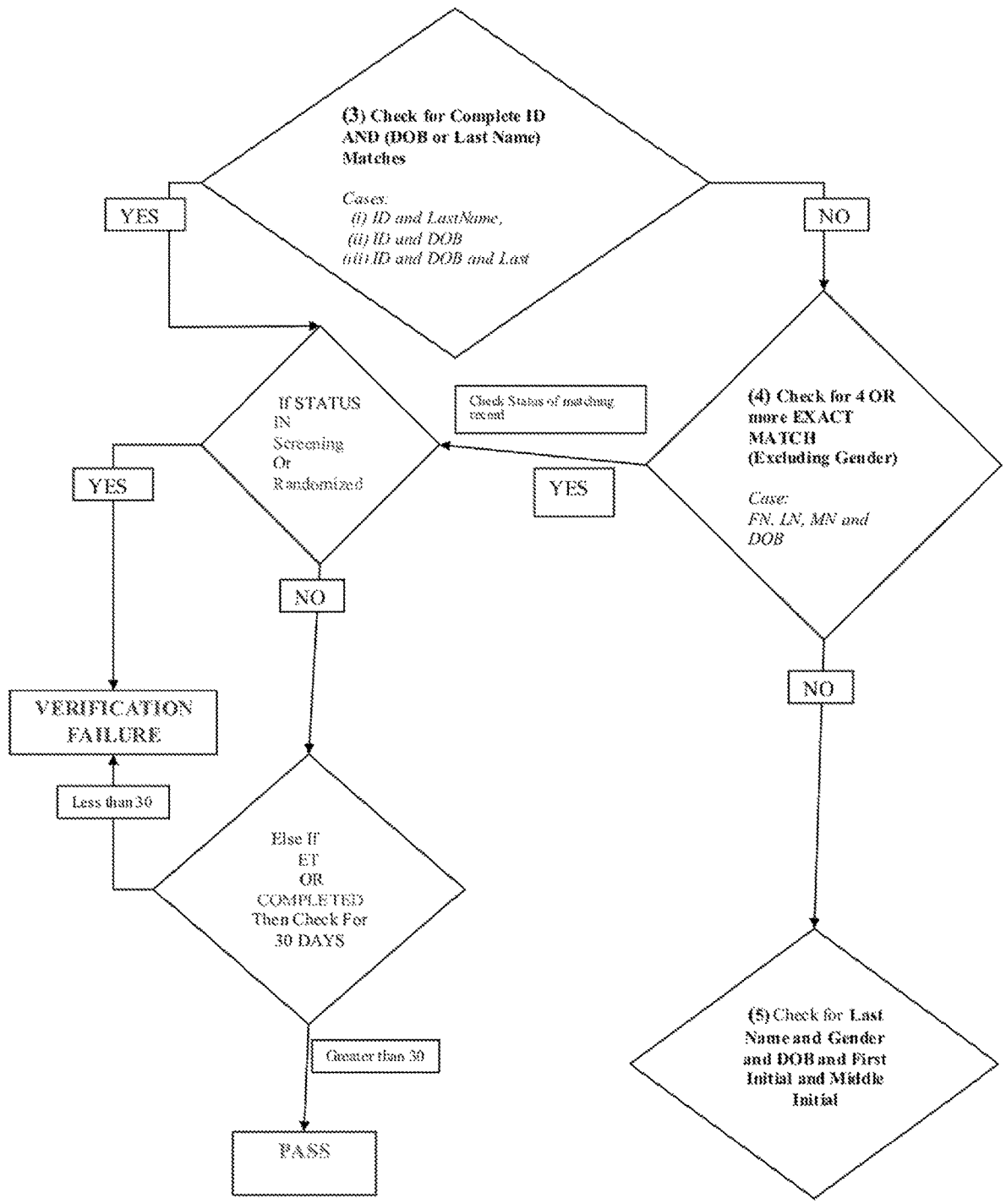
FIG. 3 is a flow chart of further steps of the method of checking participant credentials.
Figure 4:
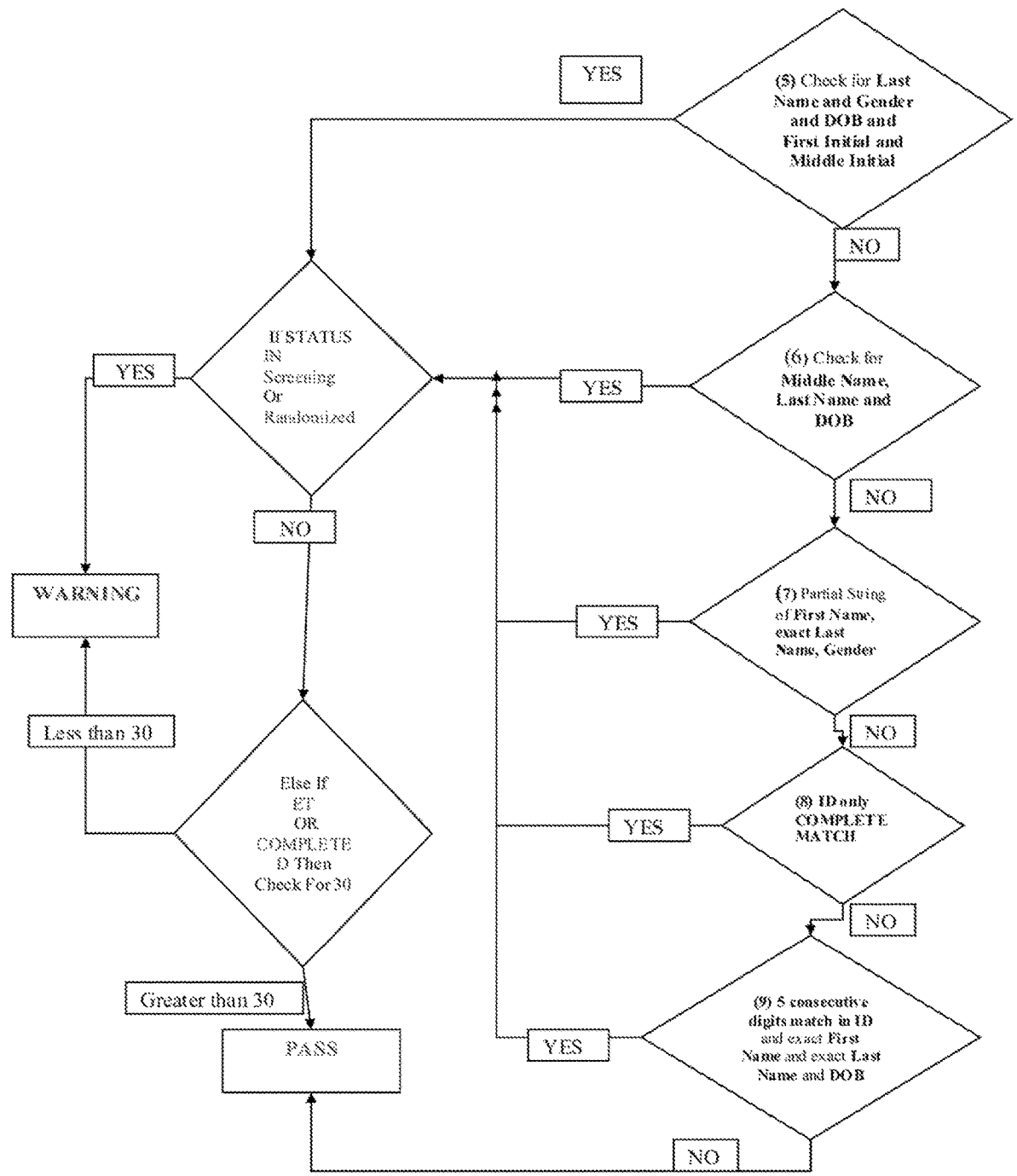
FIG. 4 is a flow chart of further steps of the method of checking participant credentials.

FIGS. 2-4 show more detailed steps in the method of screening participants for the clinical trials. Each of these steps can be modified as necessary for a particular trial. TABLE 1 below summarizes the various steps of inputs, outputs, and rules violated. Failure Rules and Warning Rules are also summarized below.

In the first step (1), it must be determined whether the patient credentials match deleted UIC's within the system. If there is a match, it is checked whether the data was entered 30 days or more. If 30 days have passed, the same UIC can be assigned to the participant and they can be entered in the trial. If it has been less than 30 days, there is a verification failure and the participant should not be entered in the trial.

If the patient credentials did not match deleted UIC's, a complete match is checked for at (2). If there is a complete match, and if the participant is in Screening or Randomized, there is a verification failure. Once a patient signs a study specific consent, they enter the screening period. In this period a series of tests are performed to see if they are eligible and meet the criteria to proceed with the study and receive the medication or treatment offered in the protocol. Randomization is the process of administering treatment, which can include placebo. At this point they are monitored for efficacy and any adverse events. Once a participant signs consent and is "in screening" they can no longer screen for or participate in another clinical trial until they either early terminate or complete the study and for at least 30 days thereafter. If the participant is not in Screening or Randomized, and ET or Completed is the case, a check is made for 30 days passing ET means early terminate for various reasons. This can be for adverse events or side effects, lack of efficacy, or competing medical issues, or simply if the subject withdraws their consent and no longer wishes to participate. Completed means they finished all planned visits of the study and will be eligible for any other study at least 30 days or more later. If less than 30 days have passed, there is a verification failure, but if 30 days or more have passed, the participant can be entered into the trial.

If there was not a complete match at (2), a check is made for complete ID and (Date of Birth (DOB) or Last Name) matches at (3) (see FIG. 3). There are several cases that could match: ID and Last Name, ID and DOB, or ID, DOB, and Last Name. If there is a match at (3), the status is checked for the participant being in Screening or Randomized, and if they are, there is a verification failure. If they are not, and ET or Completed is the case, a check is made for 30 days passing. If less than 30 days have passed, there is a verification failure, but if 30 days or more have passed, the participant can be entered into the trial.

If a match was not made at (3), a check is made for 4 or more Exact Matches (excluding gender), such as First Name (FN), Last Name (LN), Middle Name (MN), and DOB at (4). If a match is found, the steps are performed the same as if a match is found at (3).

If a match is not found at (4), then a check is made for a match of Last Name, Gender, DOB, First Initial, and Middle Initial at (5) (see FIG. 4). If there is a match, the status is checked for the participant being in Screening or Randomized, and if they are, there is a Warning. A Warning means that there are many identifiers in the information that are not an exact match of the UIC. For instance, if there is a typographical error and a wrong birthdate is put in to the system, or if the name is not entered exactly then an amber colored warning banner can appear on the screen. It states that there are many portions of information that very closely resemble a subject already in the database and to please make sure there are no errors. The study coordinator or individual entering the data can make the choice if this indeed not a match or is a match and thereby resulting in a Verification Success or pass, or Verification Failure. If the participant is not in Screening or Randomized, and ET or Completed is the case, a check is made for 30 days passing. If less than 30 days have passed, there is a Warning, but if 30 days or more have passed, the participant can be entered into the trial.

If a match is not found at (5), then a check is made for a match of Middle Name, Last Name, and DOB at (6). If there is a match, the steps are performed the same as if a match is found at (5).

If there is not a match at (6), a check is made for a match of Partial String of First Name, exact Last Name, and Gender at (7). If there is a match, the steps are performed the same as if a match is found at (5).

If there is not a match at (7), a check is made for a match of ID only being a complete match at (8). If there is a match, the steps are performed the same as if a match is found at (5).

If there is not a match at (8), a check is made for a match of 5 consecutive digits of the ID, exact First Name, exact Last Name, and DOB at (9). If there is a match, the steps are performed the same as if a match is found at (5). If there is not a match, then the participant can be entered into the trial.

TABLE 1

| Sr. No | Input | Output | Rule Violated |
|---|---|---|---|
| 1 | Complete Id AND DOB | Failure | #3 |
| 2 | Complete Id AND Last Name | Failure | #3 |
| 3 | Complete Id AND First Name | Warning | Not tracked by any Rule |
| 4 | Complete Id AND Middle Name | Warning | Not tracked by any Rule |
| 5 | Complete Id AND Gender | Warning | Not tracked by any Rule |
| 6 | Complete Id AND Initials | Warning | Not tracked by any Rule |
| 7 | First Name, Last Name, Middle Name and DOB | Failure | #4 |
| 8 | First letter of First Name, First Letter of Middle Name, complete Last Name, Gender AND DOB | Warning | #5 |
| 9 | Complete Middle Name, Complete Last Name AND DOB | Warning | #6 |
| 10 | First 3 letters of First Name, complete Last Name, Gender AND DOB | Warning | #7 |
| 11 | Only ID Number completely Matches | Warning | #8 |
| 12 | 5 consecutive digits in ID, complete First Name, Complete Last Name AND DOB | Warning | #9 |
| 13 | 5 consecutive digits in ID AND First Initial | Pass | |
| 14 | 5 consecutive digits in ID AND Complete First Name | Pass | |
| 15 | 5 consecutive digits in ID AND Complete Last Name | Pass | |
| 16 | 5 consecutive digits in ID AND Complete Middle Name | Pass | |
| 17 | 5 consecutive digits in ID AND Gender | Pass | |
| 18 | 5 consecutive digits in ID AND DOB | Pass | |
| 19 | First Initial, Complete Middle, Complete Last AND Gender | Pass | |
| 20 | All Credentials not matching | Pass | |
| 21 | First Initial, middle initial, last initial and DOB | Pass | |
| 22 | First Initial, middle initial, last initial and gender | Pass | |

Failure Rules:

Rule 1: If UIC matches with a deleted Subject, Then check if the 30 days have been past its deletion, If yes then PASS, otherwise FAILURE Rule 2: All Credentials Complete Match Rule 3: [Complete ID and DOB] OR [Complete ID and Last Name]

Rule 4: 4 or More Exact Match excluding Gender.

Warning Rules:

Rule 5: First Initial and Middle Initial and exact Last name and Gender and DOB

Rule 6: exact Middle Name and exact Last Name and DOB

Rule 7: Partial string matches in First Name and exact Last Name and Gender and DOB Rule 8: Complete ID Only Rule 9: 5 consecutive digits in ID and exact First Name and exact Last Name and DOB

EXAMPLE 2

The following is an example of an algorithm used to encrypt and decrypt data.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology, which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

What is claimed is:

1. A method of screening participants for a clinical trial, including the steps of:

obtaining identifying information from a prospective participant chosen from the group consisting of a biometric sample, personal information, physical attributes, and combinations thereof;

populating a database server with the identifying participant information and storing the information on non-transitory computer readable media;

accessing a screening mechanism in electronic communication with the database server and screening the participant for the clinical trial based on the participant information and the screening mechanism searching for a match with existing participant information in the database server and a plurality of outside databases to determine protocol violations, wherein the outside databases include each of clinical trial databases, IVRS/IWRS databases, screening/dosing logs, clinical trial management systems (CTMS), databanks that have research subject information, databanks that have information regarding drug/medication use, blood product donation databases, sperm banks, and human by-product databases, and wherein the protocol violations include each of the prospective participant currently being in-screening at the same or another research site, the prospective participant violating the required number of half lives since the last research trial, the prospective participant violating the washout period in between trials, the prospective participant violating a biologic modifier washout period, the prospective participant exposed to the same investigational compound if exclusionary per the protocol, the prospective participant has exceeded the maximum number of clinical trials per period of time, the prospective participant already was a screen failure for the same trial if exclusionary, the prospective participant has a blood draw violation, the prospective participant has a plasma draw violation, and the last visit of the prospective participant is in violation of protocol;

electronically alerting a research site or clinical trial administration if the participant is found to have matching information to existing participant information in the database server or outside databases based on the screening mechanism, wherein electronically alerting comprises determining if the participant is enrolling in the clinical trial multiple times, enrolling in multiple clinical trials at once, enrolling in the clinical trial sooner than a specified mandatory washout period between the clinical trials, or if any of the protocol violations occur; and determining eligibility of the participant for the clinical trial and preventing the protocol violations.

2. The method of claim 1, wherein the identifying information is a biometric sample chosen from the group consisting of hair, saliva, urine, blood, plasma, iris scan, photograph or facial recognition, a voice recording, fingerprints, and palm vein scans and combinations thereof.

3. The method of claim 1, wherein the identifying information is personal information chosen from the group consisting of first name, middle name, last name, date of birth, gender, government issued identification, and combinations thereof.

4. The method of claim 3, further including, after said obtaining step, the step of obtaining government issued identification and assuring that the participant is responsible for taxes incurred for stipend disbursements.

5. The method of claim 3, further including, after said obtaining step, the step of obtaining and validating government issued identification for criminal backgrounds and sex offender status.

6. The method of claim 1, wherein the identifying information is physical attributes chosen from the group consisting of height, weight, hair color, eye color, facial recognition, and combinations thereof.

7. The method of claim 1, wherein the participant information is chosen from the group consisting of history of participation in other clinical trials, status of current enrollment or prospective enrollment in clinical trials, the study start and end dates of the other clinical trials, the sponsor and sponsor information for the other clinical trials, the trial site, contact person, protocol identifier, study number, and combinations thereof.

8. The method of claim 1, wherein said screening step further includes the step of entering the participant into the clinical trial if no matching existing participant information is found.

9. The method of claim 8, further including the step of the system sending reminders to participants regarding upcoming visits for the clinical trial.

10. The method of claim 1, further including the step of generating reports from information in the database server.

11. The method of claim 1, further including the step of the participant receiving a communication chosen from the group consisting of safety communications, new study related instructions, recruitment for new studies, data or study results with regards to dose and efficacy of the investigational treatment, engagement of the participant, and combinations thereof.

12. The method of claim 1, wherein said obtaining step utilizes a system chosen from the group consisting of an IVRS (interactive voice response system) and an IWRS (interactive web response system).

13. The method of claim 1, further including the step of notifying research site and verified clinical trial administration if prospective participants are determined to be violating protocol.

14. The method of claim 1, wherein said screening step further includes accessing and pulling all data and unifying the data in the database server and the outside databases to perform said screening step.

15. The method of claim 1, further including, after said obtaining step, the steps of generating a unique identifier code, populating the database server with the unique identifier code, and screening the participant for the clinical trial based on the unique identifier code.

16. A system for screening participants for a clinical trial, comprising:

an electronic database server in electronic communication with a server instance for collecting participant information on non-transitory computer readable media, said server instance including a screening mechanism for determining eligibility of the participant for the clinical trial and preventing protocol violations and being in electronic communication with a plurality of outside databases including each of clinical trial databases, IVRS/IWRS databases, screening/dosing logs, clinical trial management systems (CTMS), databanks that have research subject information, databanks that have information regarding drug/medication use, blood product donation databases, sperm banks, and human by-product databases, wherein said protocol violations include each of the prospective participant currently being in-screening at the same or another research site, the prospective participant violating the required number of half lives since the last research trial, the prospective participant violating the washout period in between trials, the prospective participant violating a biologic modifier washout period, the prospective participant exposed to the same investigational compound if exclusionary per the protocol, the prospective participant has exceeded the maximum number of clinical trials per period of time, the prospective participant already was a screen failure for the same trial if exclusionary, the prospective participant has a blood draw violation, the prospective participant has a plasma draw violation, and the last visit of the prospective participant is in violation of protocol, and said server instance including an alerting mechanism for electronically alerting a research site or clinical trial administration if the participant is found to have matching information to existing participant information in said electronic database server or outside databases based on said screening mechanism, wherein said alerting mechanism determines if the participant is enrolling in the clinical trial multiple times, enrolling in multiple clinical trials at once, enrolling in the clinical trial sooner than a specified mandatory washout period between the clinical trials, or if any of the protocol violations occur, and said system determining eligibility of the participant for the clinical trial and preventing the protocol violations.

17. The system of claim 16, further including a unique identifier code generator, a report generating mechanism and a communication mechanism for communicating with trial participants, and wherein said electronic database collects unique identifier codes generated.

* * * * *